United States Patent [19]

LeVeen

[11] 4,154,246

[45] May 15, 1979

[54] FIELD INTENSIFICATION IN RADIO FREQUENCY THERMOTHERAPY

[76] Inventor: Harry H. LeVeen, 800 Poly Pl., Brooklyn, N.Y. 11209

[21] Appl. No.: 818,502

[22] Filed: Jul. 25, 1977

[51] Int. Cl.² ............................................. A61N 1/40
[52] U.S. Cl. .................................. 128/784; 128/786; 128/804
[58] Field of Search .......... 128/413, 404, 405, 419 R, 128/419 F, 422, 399, 401, 1.3–1.5, 407

[56] References Cited

U.S. PATENT DOCUMENTS

| 2,515,683 | 7/1950 | Acosta | 128/422 |
|---|---|---|---|
| 3,230,957 | 1/1966 | Seifert | 128/407 |
| 3,566,877 | 3/1971 | Smith | 128/422 |
| 3,890,953 | 6/1975 | Kraus et al. | 128/1.5 |
| 3,915,151 | 10/1975 | Kraus | 128/1.5 |
| 4,028,518 | 6/1977 | Boudouris et al. | 128/413 X |
| 4,030,480 | 6/1977 | Meyer | 128/1.5 |

FOREIGN PATENT DOCUMENTS

| 559353 | 9/1932 | Fed. Rep. of Germany | 128/413 |
|---|---|---|---|
| 1143937 | 2/1963 | Fed. Rep. of Germany | 128/404 |
| 1284528 | 12/1968 | Fed. Rep. of Germany | 128/1.5 |
| 353231 | 7/1931 | United Kingdom | 128/413 |

OTHER PUBLICATIONS

LeVeen et al., "Tumor Eradication . . . Therapy", JAMA, May 17, 1976, vol. 235, No. 20.

*Primary Examiner*—Lee S. Cohen
*Attorney, Agent, or Firm*—Brooks, Haidt, Haffner & Delahunty

[57] ABSTRACT

A technique in the treatment of tumors in humans utilizing radio frequency electromagnetic radiation to produce necrosis of the tumors by which intensification at the situs of the tumor of a radio frequency field applied across the portion of the body containing the tumor is obtained by positioning a small inductance element preferably in the form of a closed resonant circuit such that the inductance is in or adjacent to the tumor tissue and thus functions to concentrate the field at that location. Alternatively, rather than utilizing a resonant circuit, the inductance can be coupled to the output of the radio frequency generator utilized and applies the radio frequency electromagnetic field.

2 Claims, 3 Drawing Figures

FIELD INTENSIFICATION IN RADIO FREQUENCY THERMOTHERAPY

This invention relates to radio frequency thermotherapy in the treatment of tumors and the like and in particular, provides a technique for intensifying the radio frequency field at the situs of the tumor in order to increase the energy absorption by the tumor and thereby increase the temperature of the tumor to enable selective necrosis of the tumor.

Radio frequency theremotherapy involves positioning a portion of the body containing a tumor in a radio frequency electromagnetic field in order to produce necrosis of the tumor. This technique is described in LeVeen U.S. Pat. No. 3,991,770.

Tumor cells are specially thermolabile. When tissue is heated by radio frequency diathermy, the heat is dissipated by the blood supply. The blood supply of tumors is exceedingly sluggish because the tumor begins to grow de novo in a pre-existing blood supply. As the tumor expands, new capillaries form in the tumor but they only make connections with capillaries at the periphery of the tumor. Thus, a high resistance vascular bed in the tumor makes connections only with a low pressure portion of the circulatory system. The major vessels of the region of the tumor are pushed away or, even if encased in tumor, do not contribute to an integrated blood supply.

Since the heat generated by radio frequency diathermy is carried away by the blood stream, the normal tissue with a good blood supply is rapidly cooled while heat is retained in the tumor. In spite of this advantage, it sometimes is not possible to capture enough energy in areas of low intensity adequately to heat the tumor. In the course of radio frequency thermotherapy for malignancies, it is thus frequently desirable and sometimes necessary to intensify the heat developed in the tumor. This is especially true in some forms of brain tumors where a considerable portion of the energy available is absorbed by the bony skull and in endo-bronchial carninoma where the tumor can be surrounded by an air gap.

It is thus the principal object of this invention to provide a technique for such intensification.

In one aspect of this invention, intensification is accomplished by implanting a sealed, sterile resonant circuit within the tumor adjacent to the tumor tissue which is resonant at the frequency utilized in the thermotherapy, usually 13.56 megahertz or lower. The presence of what in effect, is a small LC tuned circuit in or adjacent to the tumor tissue is to intensify radio frequency field in the vicinity of the circuit as the circuit resonates and generates electromagnetic waves.

An alternative arrangement providing similar intensification at the location of the tumor is to implant an inductance element of small suitable size which is externally connected to the radio frequency generator such that the field is concentrated at the location of the inductance which is desirably in or adjacent to the tumor tissue. While the word "implant" may imply surgical implantation, it should be understood that "implant" is meant to include the alternative mode of utilizing the resonant circuit or inductance element to cause intensification of the tumor by mounting the device on the end of a catheter which is relatively flexible and inert. This arrangement is particularly suitable for insertion into the bladder, prostate, esophagus, bronchus, sinus and other tubular organs during therapy. Surgical implantation can also be desirable where repeated thereapy is required.

For more complete understanding of the practical application of the principles of this invention, reference is made to the appended drawings in which.

Figure 1:
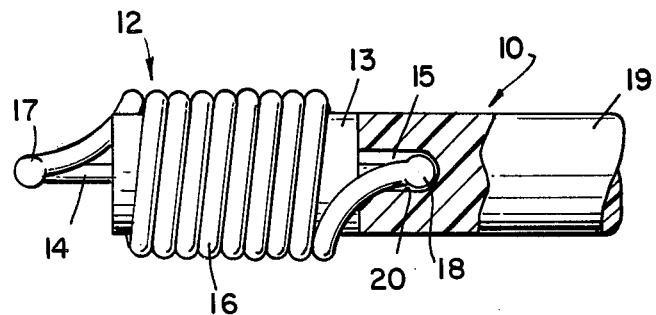
FIG. 1 is a partially sectioned elevation of a portion of a device utilized in accordance with this invention.

Referring more particularly to FIG. 1, the reference numeral 10 designates a catheter-like device suitable in conjunction with radio frequency thermotherapy for insertion into the bronchus or other similar organ to locate a resonant circuit device 12 adjacent to tumor tissue in the bronchus or the like for the purpose of intensifying the field in the vicinity of the tumor during radio frequency thermotherapy. Device 12 basically includes a tubular capacitor 13 suitable for use at radio frequency, such as 13.56 megahertz, having end leads 14 and 15 and about which a coil 16 is wound with the ends of the coil soldered at 17 and 18 to the leads 14 and 15 of capacitor 13. Resonant circuit 12 is adjusted such that the inductance of its coil portion 16 and the capacitance of its capacitor 13 are resonant at the radio frequency utilized in the diathermy treatment.

The assembly of device 12 is mounted on a rod 19 of nylon or similar solid dielectric material to complete device 10 by recessing the end of rod 19, as indicated at 20, to receive soldered lead 15 and the end of coil 16 with the adjacent end of rod 19 adhesively bonded to the adjacent end of capacitor 13, for example, by heating the end of rod 19 sufficiently to render it thermoplastic and then cooling. After assembling device 12 with rod 19 to form catheter-type device 10, the end of device 10 which includes device 12 is suitably coated with polyurethane resin or the like to fill all open intersteses and present a smooth outer configuration Before use, of course, the device 12 is suitably sterilized and is then inserted into the bronchus or other region where the tumor to be treated is located such that the device 12 is adjacent to the tumor. Thereafter, the portion of the body containing the tumor is then treated with radio frequency electromagnetic energy by locating that portion of the body in a field of such energy, having a frequency at which device 12 resonates.

Figure 2:
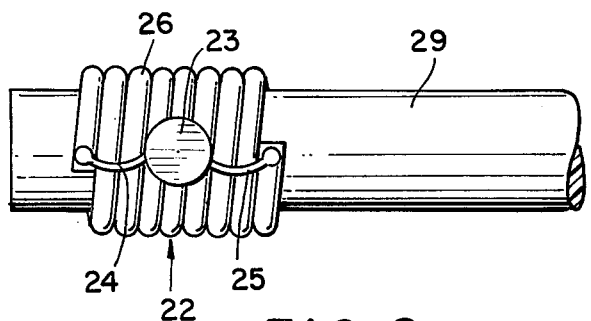
FIG. 2 is a similar view in elevation of a portion of another device in accordance with this invention.

FIG. 2 shows a variation of the structure of FIG. 1 wherein a solid dielectric rod 29 forms the base for the resonant circuit device 22. Resonant circuit device 22 is formed utilizing a coil 26 tightly wound about the end of rod 29 with the ends of coil 26 connected to the leads 24 and 25 of a disc capacitor 23 positioned alongside coil 26. The inductance of coil 26 and capacitance of capacitor 23 are selected such that device 22 is resonant at the frequency to be utilized in therapy. Again, the device is suitably coated with polyurethane resin or the like to present a smooth, void-free exterior.

Device 22 of FIG. 2 is utilized in a similar manner to device 2 of FIG. 1.

Figure 3:
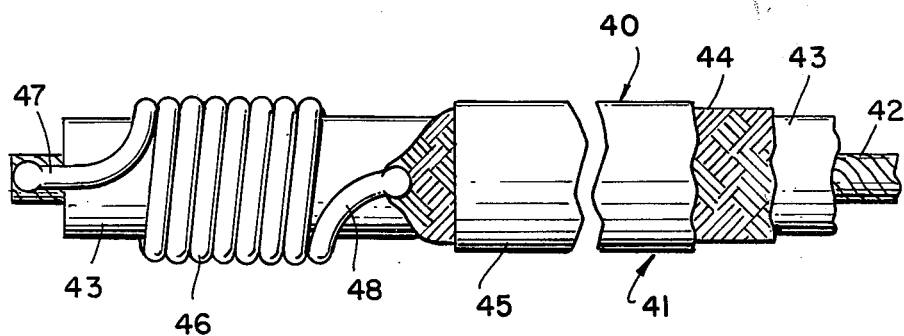
FIG. 3 is an elevation of yet another device utilized in accordance with this invention.

Referring to FIG. 3, there is shown a modification in which a catheter-type device 40 is adapted to produce a radio frequency electromagentic field within the body of a person being treated. In this case, device 40 includes a slender elongated cable 41 including a central conductor 42 and solid insulation 43 about such central conductor. A braided metallic shield 44 is applied over insulation 43 and over that a jacket 45. Typically insulation 43 is polytetrafluorethylene applied to conductor 42 by extrusion and sintering, and jacket 45 is tape-wrapped polytetraflourethylene insulation. At one end (left in FIG. 3) jacket 45 and braid 44 are stripped off the underlying insulation 43 and a coil 46 of copper or preferably silver-coated copper is helically applied about the bared insulation 43. At one end 47, coil 46 is connected to conductor 42, and at the other end 48, coil 46 is connected to braid 44 such that the inductance formed by coil 46 is connected between metallic braid 44 and conductor 42.

In use device 40 is inserted with coil 46 leading into a body cavity such as the bronchus to locate coil 46 adjacent a tumor which is to be treated. Conductor 42 and braided shield 44 are connected across the output of a radio frequency generator with suitable impedance matching to maximize output. The generator is then energized to cause coil 46 to generate a radio frequency electromagnetic field adjacent to the tumor.

EXAMPLE NO. 1

A patient with carcinoma of the lung and endobronchial disease close to the pulmonary hilus is treated by radio frequency thermotherapy utilizing 4-inch diameter copper electrodes placed anteriorly and posteriorly over the tumor mass. Bronchoscopy is done prior to the therapy. A 1½ inch tuned circuit of the type shown in FIG. 2, is wound around one end of a two foot nylon rod ⅛" in diameter. The rod allows the tuned circuit to be introduced through the bronchoscope to the exact area of the disease. The bronchoscope is then removed leaving the tuned circuit in the bronchus during a three hour therapy period. The electrodes on anterior and posterior surface of the chest are activated with 150 to 200 watts of energy at 13.56 megahertz at which the circuit is resonant. The focal point of the energy is now in the region of the tuned circuit.

EXAMPLE NO. 2

A carcinoma of the esophagus is treated with a 2" coil of the type described in FIG. 3 wound around and attached to the end of a coaxial cable of approximately ⅛" in diameter. The coil is introduced into the esophagus through the mouth, and its position is checked by x-ray. The tuned circuit is then activated through the coaxial cable with a radio frequency electrical signal at 13.56 megahertz. Approximately 75 watts are utilized to treat the local lesion for a period of three hours. After therapy, the tuned circuit is removed by pulling on the coaxial cable which protrudes from the mouth.

I claim:

1. In the process of treating a naturally occurring tumor in a human by positioning the portion of the body containing the tumor in a radio frequency electromagnetic field thereby to heat the tumor tissue in said portion of said body by adsorption of energy from said radio frequency electromagnetic field for a period of time and with intensity sufficient to cause necrosis of the tumor, but insufficient to cause significant damage to the adjacent normal tissue in said field, the improvement which includes implanting an inductance element in the vicinity of said tumor which is part of a circuit tuned to the frequency of said field thereby to increase the intensity of said field in the vicinity of said tumor.

2. A method according to claim 1 in which said radio frequency is 13.56 Megahertz.

* * * * *